US012447085B2

(12) United States Patent
Quast et al.

(10) Patent No.: US 12,447,085 B2
(45) Date of Patent: Oct. 21, 2025

(54) PROTECTIVE BARRIER SYSTEM AND METHOD OF USING SAME

(71) Applicant: AER SUPPLY CONCEPTS LTD., New Westminster (CA)

(72) Inventors: Ryan Patrick Quast, Vancouver (CA); Jennifer Teresa Cane, New Westminster (CA); Babak Golkar, North Vancouver (CA)

(73) Assignee: AER SUPPLY CONCEPTS LTD.

( * ) Notice: Subject to any disclaimer, the term of this patent is extended or adjusted under 35 U.S.C. 154(b) by 1070 days.

(21) Appl. No.: 17/238,379

(22) Filed: Apr. 23, 2021

(65) Prior Publication Data

US 2021/0330534 A1 Oct. 28, 2021

Related U.S. Application Data

(60) Provisional application No. 63/015,273, filed on Apr. 24, 2020.

(30) Foreign Application Priority Data

Apr. 24, 2020 (CA) ...................................... 3079510

(51) Int. Cl.

| | |
|---|---|
| ***A61G 10/00*** | (2006.01) |
| ***A61B 46/23*** | (2016.01) |
| ***A61B 90/00*** | (2016.01) |
| ***A61B 90/40*** | (2016.01) |
| *A61M 16/00* | (2006.01) |
| *A61M 16/06* | (2006.01) |

(52) U.S. Cl.

CPC ............ *A61G 10/005* (2013.01); *A61B 46/23* (2016.02); *A61B 90/05* (2016.02); *A61B 90/40* (2016.02); *A61M 16/0084* (2014.02); *A61M 16/06* (2013.01)

(58) Field of Classification Search

CPC ......... A61B 46/20; A61B 46/23; A61B 90/05; A61B 90/40; A61G 10/005; A61M 16/0488; A61M 16/049; A61M 16/0493; A61M 16/06

See application file for complete search history.

(56) References Cited

U.S. PATENT DOCUMENTS

| | | | | |
|---|---|---|---|---|
| 2013/0172768 A1* | 7/2013 | Lehman | A61M 16/06 128/205.25 |
| 2017/0325780 A1* | 11/2017 | Neto | A61B 46/10 |
| 2019/0381265 A1* | 12/2019 | Banuelos | A61M 16/0084 |
| 2021/0299383 A1* | 9/2021 | Molnar | A61B 90/05 |
| 2021/0330922 A1* | 10/2021 | Boston | A61M 16/0683 |

* cited by examiner

*Primary Examiner* — Keri J Nelson

(74) *Attorney, Agent, or Firm* — Field LLP; Michael Sharp

(57) ABSTRACT

A protective barrier system that blocks and prevents infectious aerosols generated by or around a supine patient from escaping into a surrounding environment and reaching and contaminating a healthcare worker treating the patient with a patient interface device. The system includes a flexible, fluid-impervious sheet that covers the patient and blocks and prevents escape of the infectious aerosols into the surrounding environment. The sheet has an aperture that is adapted to enables access to the patient and couple to the interface device without gapping for blocking of the infectious aerosols and operative positioning of the system over and on the patient. A corresponding method is also disclosed.

11 Claims, 6 Drawing Sheets

PROTECTIVE BARRIER SYSTEM AND METHOD OF USING SAME

CROSS REFERENCE TO RELATED APPLICATIONS

This application claims priority from U.S. Provisional Patent Application No. 63/015,273 and Canadian Patent Application No. 3,079,510, both filed on Apr. 24, 2020 and entitled "Droplet Protective Cover", entireties of which are incorporated herein by reference.

FIELD

Embodiments described herein relate to containment and preventing spread of infectious aerosols. More particularly, embodiments described herein relate to a system which provides an additional layer of protection to health care workers from infectious aerosols generated by or around a patient. A corresponding method is also described.

BACKGROUND

First responders are routinely attending to emergency health events such as cardiac arrest, trauma, drug overdose, chemical exposure, etc in a non-clinical setting. First responders provide basic care and comfort to a patient until the arrival of Emergency Medical Services (EMS) or higher level of care. Aerosol-generating medical procedures such as manual resuscitation using a manual resuscitator, such as an Ambu® Resuscitator manufactured by Ambu, Inc., USA and Ambu A/S, Denmark, are routinely performed by first responders in non-clinical settings. These procedures require close proximity to a patient. Typically, first responders wear a surgical mask and gloves while performing these aerosol-generating medical procedures. While surgical masks may provide protection against most infectious aerosols, modelling studies have shown that surgical masks provide little to no protection against the SARS-CoV-2 aerosols. Further, studies have shown that the SARS-CoV-2 aerosols are immediately respirable, suggesting the need for improved protection for persons working in close proximity to patients with potentially the SARS-CoV-2 virus. Guidance to health care workers including first responders, during the global pandmenic of COVID-19, is that all patients should be treated as infected until determined otherwise.

In a resource rich environment such as a medical or hospital setting, aerosol-generating medical procedures are performed on a patient after the patient has been placed within an enclosure that contains and prevents aerosol spread. Typically, the enclosure is a collapsible dome or tent that is erected around the patient. Generally the tent consists of a clear plastic sheet supported on a metal framework. The tent encloses at least a patient's upper torso and contains aerosols generated around the patient within it thereby preventing their spread into the surrounding environment. The tent has precut openings that allow access to the patient for procedures. Applicant believes that use of tents to contain aerosol spread in a non-clinical setting may not be feasible for reasons set out below. The tent, when erected, occupies a large footprint as it is generally sized to cover at least a patient's upper torso. Space constraints are common in non-clinical settings and, therefore, many times, there might just not be the space to erect the tent in such settings. Further, even in a collapsed state, the tent is relatively large in size thereby making its portability difficult. The tent is expensive due to multiple components. Furthermore, in some instances the metal framework of the tent might also pose a potential risk to the patient. For example, it is not uncommon for drug overdose patients to flail aggressively as they are being revived. In such instances, the metal framework of the tent can cause serious injuries to the patient.

There is consequently a need for a system and method whereby spread of infectious aerosols can be effectively prevented in a non-clinical setting in a simple, inexpensive and safe manner, and for a system which is lightweight, easy to handle and dispose of after use.

SUMMARY

Accordingly, in one embodiment a protective barrier system is provided. The system prevents spread of infectious aerosols, generated by or around a patient, into a surrounding environment when the patient is in a supine position and is being treated by a healthcare worker with a patient interface device. The system comprises a flexible, fluid-impervious sheet which has preset longitudinal and transverse dimensions. The sheet is adapted to cover at least an upper torso of the patient and has a face portion which is adapted to cover at least a face of the patient. The face portion has an aperture which is adapted and dimensioned to, overlie at least a nose and mouth area of the patient, enable passage of at least a section of the interface device through it, and form a snug engagement with the section of the interface device without gapping. In use, when the sheet is positioned over and on the patient with the sheet covering at least the patient's upper torso including the face portion covering at least the patient's face and the aperture overlying at least the patient's nose and mouth area, and the section of the interface device is positioned through the aperture, the sheet and the snug engagement between the aperture and the section of the interface device block the infectious aerosols generated by or around the patient so as to prevent escape of the infectious aerosols into the surrounding environment and consequent contamination of the healthcare worker thereby forming a protective barrier between the patient and the healthcare worker.

Accordingly, in another embodiment a method for preventing spread of infectious aerosols, generated by and around a patient, into a surrounding environment when the patient is in a supine position and is being treated by a healthcare worker with a patient interface device is provided. The method comprises covering at least an upper torso of the patient with a fluid-impervious sheet such that a face portion of the sheet covers at least a face of the patient. The sheet has preset longitudinal and transverse dimensions. The method further comprises aligning an aperture in the face portion of the sheet with at least a nose and mouth area of the patient and enabling passage of at least a section of the interface device through the aperture. Further, the method comprises forming a snug engagement between the aperture and the section of the interface device without gapping and using the sheet and the snug engagement between the aperture and the section of the interface device to block the infectious aerosols generated by and around a patient so as to inhibit escape of the infectious aerosols into the surrounding environment and consequent contamination of the healthcare worker by the infectious aerosols.

DETAILED DESCRIPTION

Embodiments described herein relate to a protective barrier system that provides an additional layer of protection to health care workers attending to or treating patients in a first-response scenario such as a non-clinical setting. The system described herein blocks and thereby prevents infectious aerosols generated by or around the patient from escaping and spreading into the surrounding environment and consequently reaching and infecting the healthcare worker. The system thus forms a protective barrier between the patient and the healthcare worker thereby providing the healthcare worker with an additional layer of protection against the infectious aerosols.

Even though the system described herein is contemplated, primarily, for use in a non-clinical setting, Applicant believes that the system can be effectively used in any setting where generation and inhalation of infectious aerosols is a concern including a clinical setting such as a hospital.

"Infectious aerosols" as used herein include a generally diminutive or lightweight body of solid, liquid or gel-like matter suspended or dispersed in a gas volume and containing a living biological source such as bacteria, fungi or viruses. They can remain suspended in a column/volume of air for long periods of time, can be carried on currents in the air, or can settle onto surfaces. Depending on size they can pose a respiratory threat and can be inhaled deep into the lung.

Figure 1:
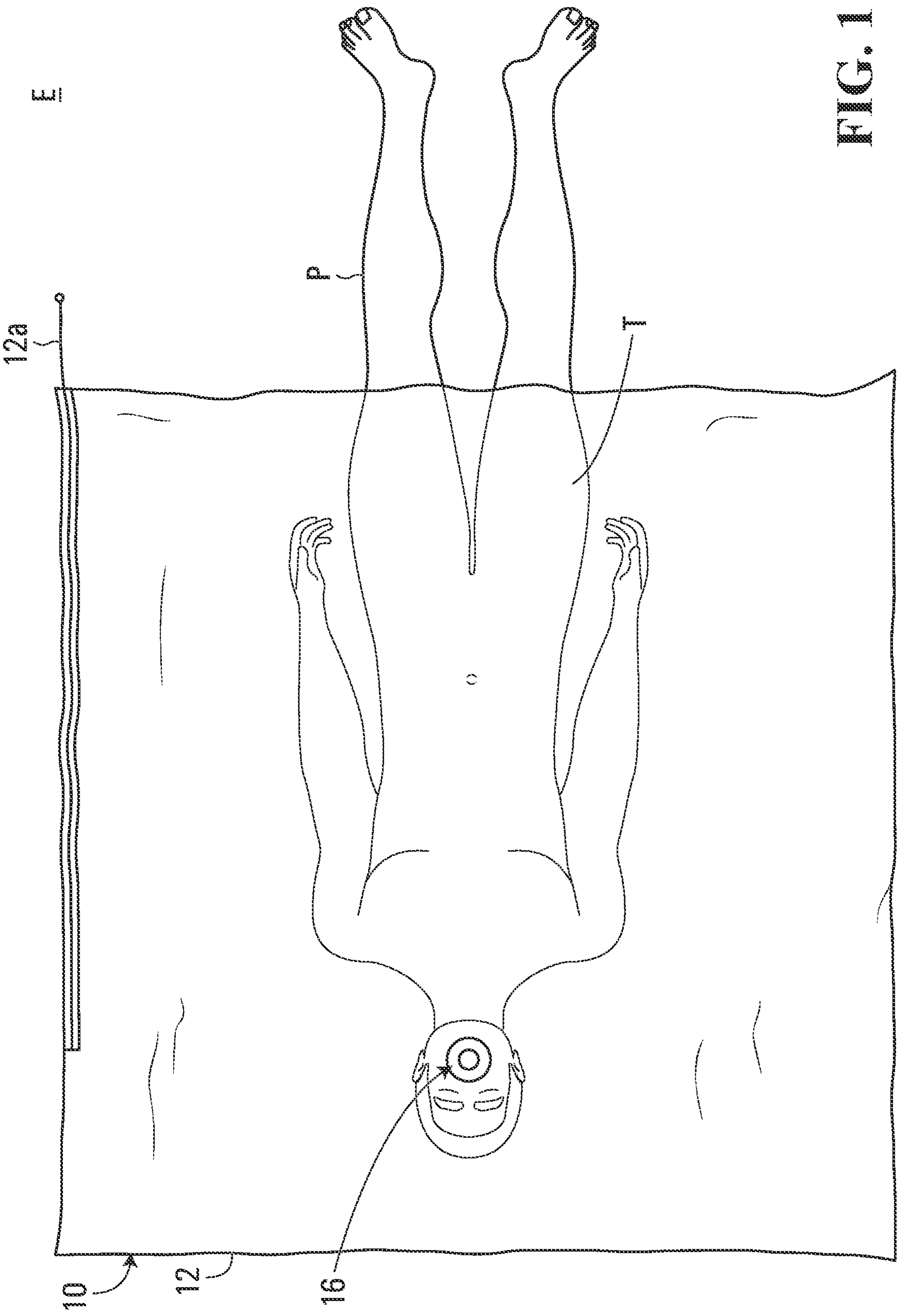
FIG. 1 is a diagrammatic top view of one embodiment of the system described herein in its use position on a patient.

FIG. 1 illustrates one embodiment of the protective barrier system described herein. In this embodiment, the system 10 comprises a flexible, fluid-impervious sheet 12 having preset longitudinal and transverse dimensions. In use, the sheet 12 is adapted to cover at least an upper torso T of a patient P in a supine position. The sheet 12 includes a face portion 14 which is adapted to cover at least a face F of the patient P. The face portion 14 has an aperture 14*a* which is adapted to overlie at least a nose and mouth area A of the patient and allow access to at least the patient's nose and mouth area in a use position of the sheet.

Various sizes of the sheet 12 are contemplated. For example, the sheet 12 may be designed to cover the entirety of a patient's body surface area or the sheet 12 may be designed to cover just an upper torso of the patient including the patient's head.

In one embodiment, the sheet 12 is a clear plastic sheet which enables the patient P to be visible to and be actively monitored by a healthcare worker (not shown) treating the patient P.

In one embodiment, the sheet 12 has a thickness of 0.05 mm to 0.8 mm.

Figure 2:
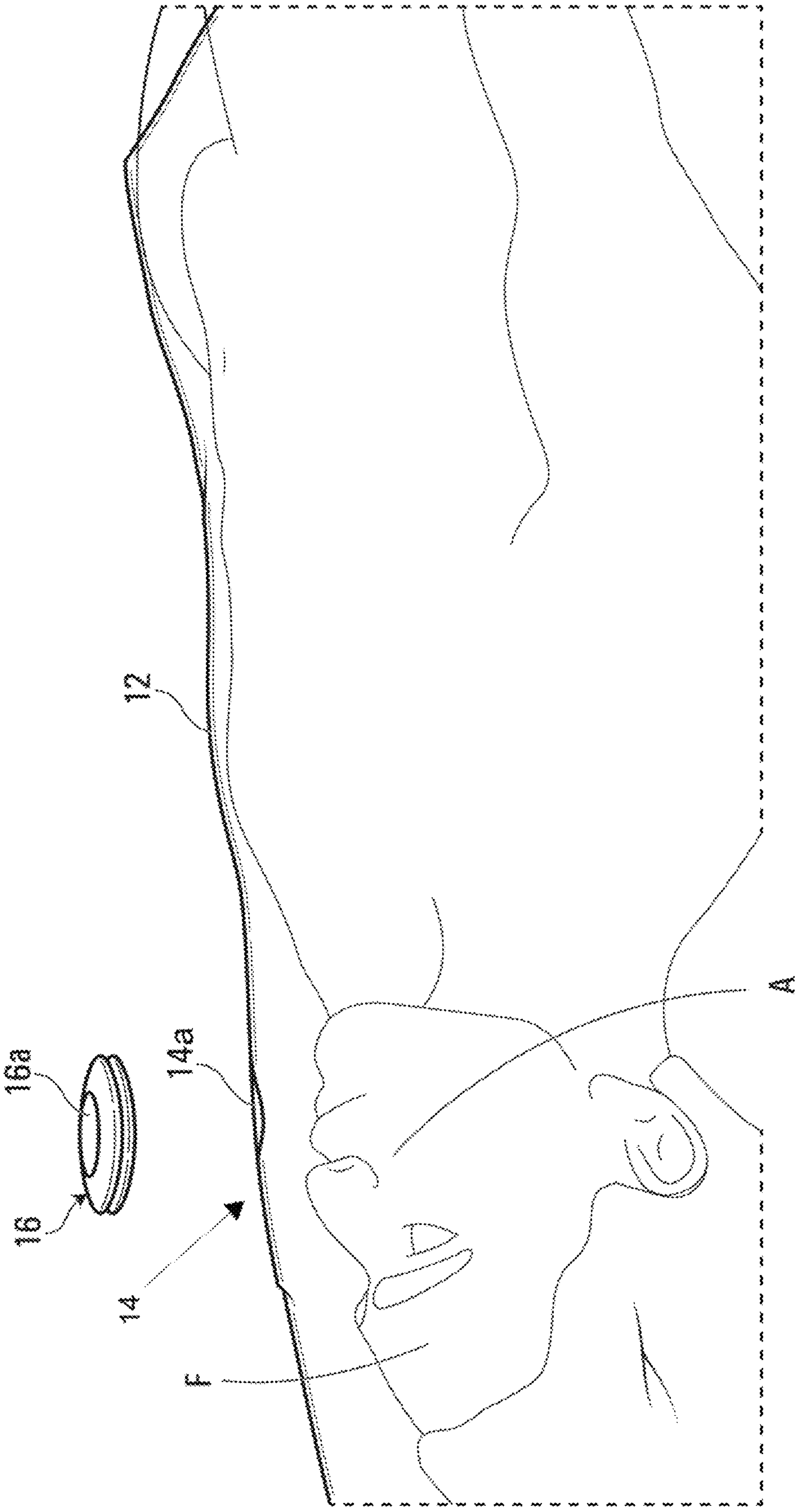
FIG. 2 is a close-up exploded view of the system of FIG. 1.
Figure 3:
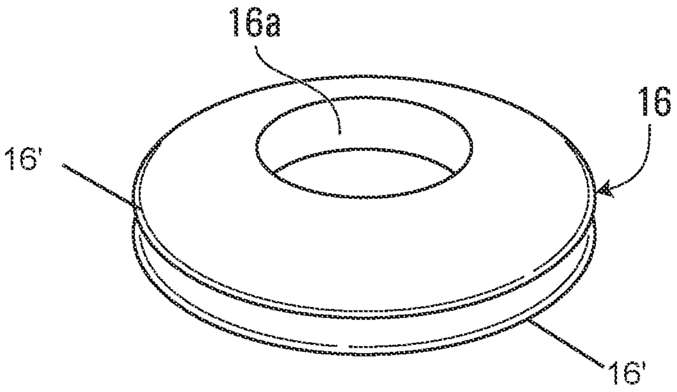
FIG. 3 is a perspective view of a plate adaptor of the system of FIG. 1.

In one embodiment and with reference to FIGS. 2 and 3, the system has a plate adaptor 16 mounted on the sheet 12 and surrounding the aperture 14*a* in the face portion 14.

In one embodiment, the plate adaptor 16 is made of a pliant non-porous material such as plastic or rubber.

In one embodiment and with reference to FIG. 3, the plate adaptor 16 encircles the aperture 14*a* and in this embodiment, the plate adaptor 16 has a corresponding aperture 16*a* which is aligned over the aperture 14*a* in the sheet 12 so as to form a sheet passageway W through the sheet 12 for allowing access to at least the patient's nose and mouth area A in a use position of the sheet 12. In the embodiment of FIG. 3, the plate adaptor 16 is a single-piece construct consisting of an upper flange and a lower flange 16'. When the plate adaptor 16 is mounted to the sheet 12, the sheet 12 is supported between the upper and lower flanges 16' with the upper and lower flanges 16' encircling the aperture 14*a* on opposite sides of the sheet 12, and the aperture 16*a* in the plate adaptor overlies the aperture 14*a* in the sheet.

Applicant has contemplated various ways of retaining the system 10 in a use position over and on the patient P. In one embodiment, the transverse dimension is selected to be greater than a width of the patient's upper torso T so as to enable the sheet 12 to be tucked under at least the patient's upper torso T for retainment of the sheet 12 over and on the patient P in the use position.

Figure 4:
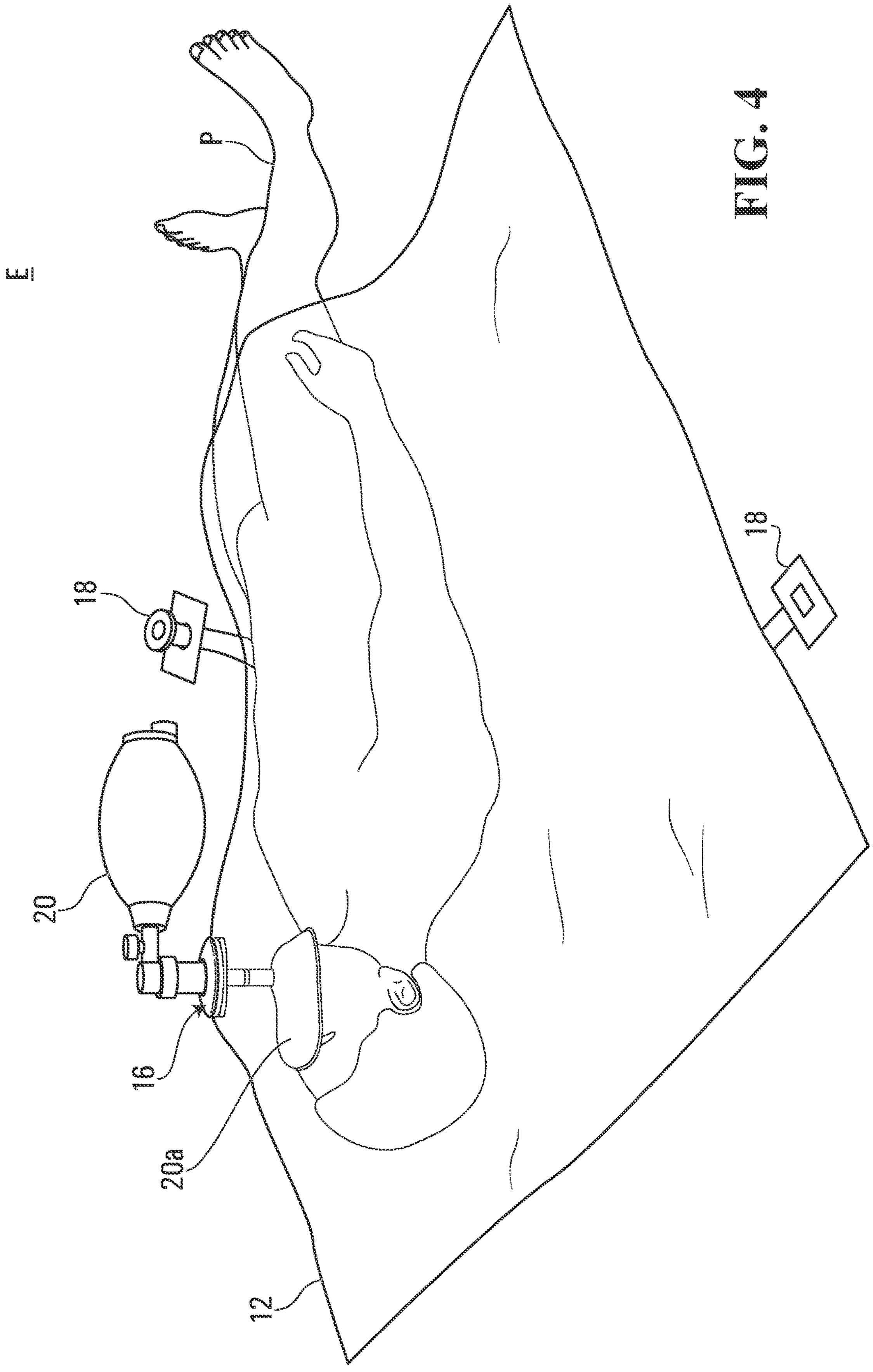
FIG. 4 is a diagrammatic illustration showing operative coupling of the system of FIG. 1 to a patient interface device and interaction of the patient interface device with the patient.
Figure 4A:
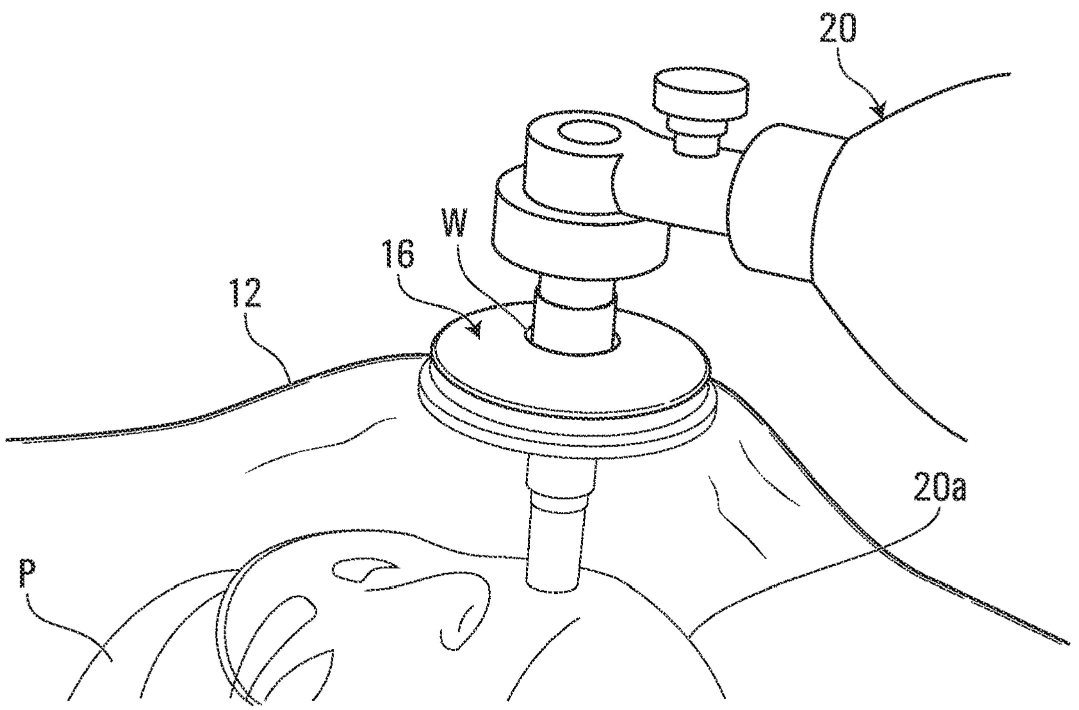
FIG. 4A is a close-up view of FIG. 4 showing the plate adaptor of the system being supported against an element of the patient interface device.

In another embodiment and with reference to FIG. 4, the sheet 12 may include one or more releasable fastener assemblies 18 having complementary components for retainment of the sheet over and on the patient in the use position.

Figure 4B:
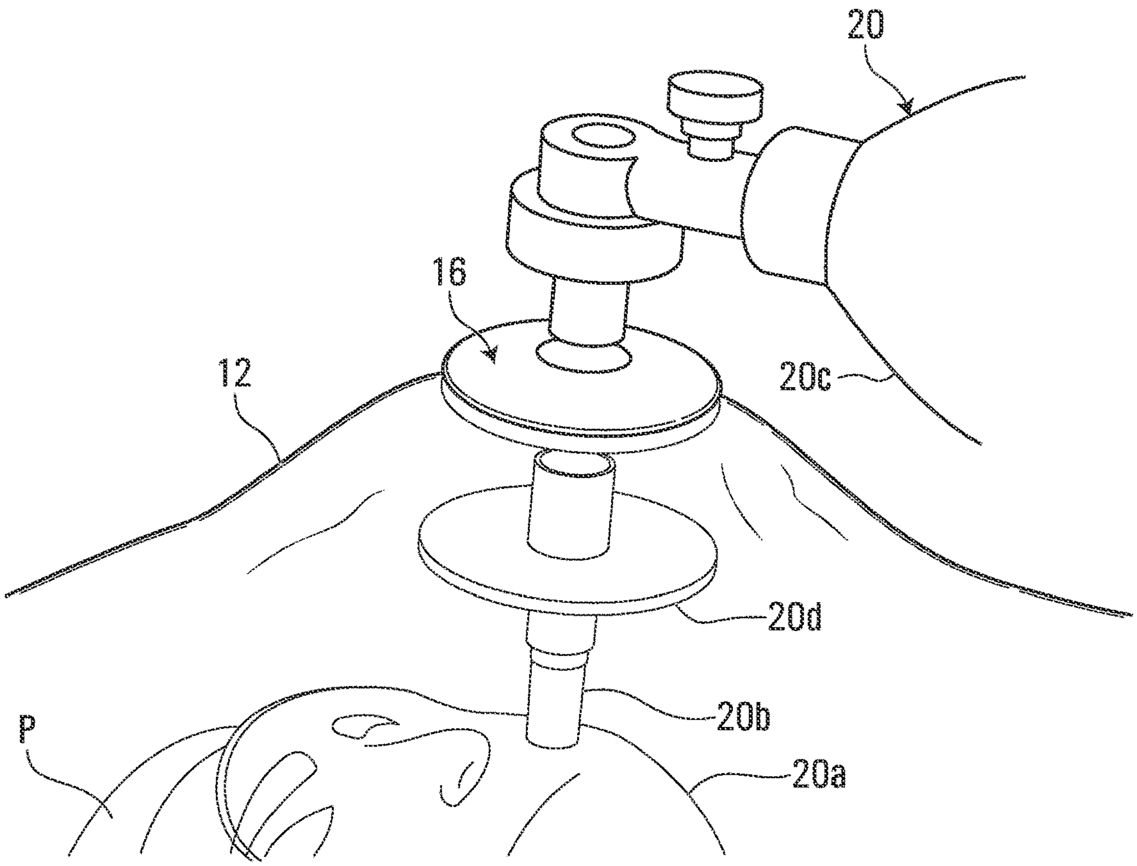
FIG. 4B is an exploded view of FIGS. 4.

In another embodiment and with reference to FIGS. 4 to 4B, the plate adaptor 16 is adapted and dimensioned to operatively couple to and be supported on a patient interface device, such as a section of a manual resuscitator 20, passing through the sheet passageway W and interacting with the patient P for retainment of the sheet 12 over and on the patient P in the use position.

In one embodiment, the pliant material of the plate adaptor 16 enables the plate adaptor 16 to allow passage of the section of the patient interface device through the sheet passageway W and to snugly engage with the section of the patient interface device regardless of the size of the section. The plate adaptor 16 snugly embraces the section of the patient interface device without gapping.

Figure 5:
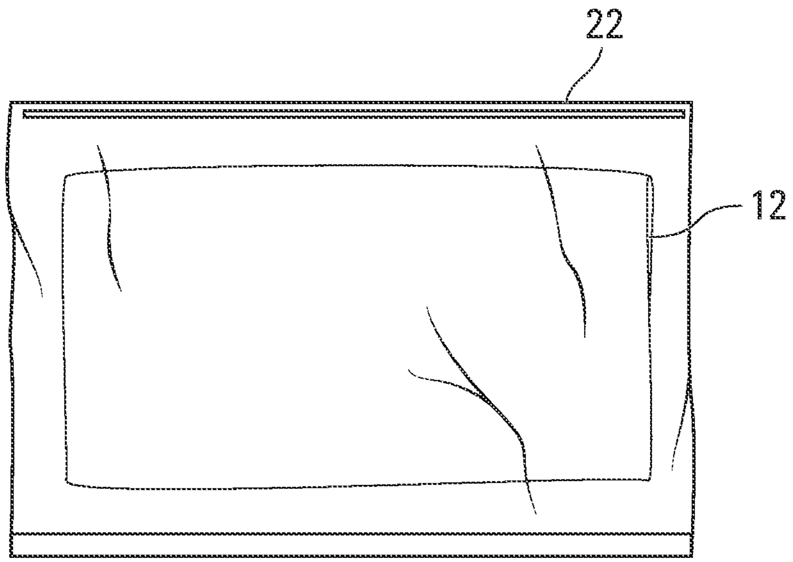
FIG. 5 is a diagrammatic illustration of a sealable bag for storing components of the system of FIG. 1, prior to and after its use.

In one embodiment and with reference FIG. 5, the system further comprises a sealable, fluid impermeable bag 22 for storing components of the system 10 prior to and after its use.

The following paragraphs describe use of the system 10 to prevent spread of infectious aerosols generated by and around a patient P into a surrounding environment E.

In a first-response scenario, a health worker (not shown), prior to attending to a patient P in a supine position, pulls the sheet 12 out from the bag 22, unfolds the sheet 12 and positions the sheet 12 on the patient P such that the face portion 14 of the sheet 12 covers the patient's face F and the sheet passageway W overlies and is aligned with least the patient's nose and mouth area A. The sheet 12 is then retained over and on the patient P by one of the methods described above. Based on testing, the above steps take less than a minute to complete.

If the patient P is a drug overdose patient, the healthcare worker may then proceed to administer an internasal medication, such as naxolone, to the patient P. The medication is administered via a syringe and tube arrangement (not shown). An end of a section of the syringe and tube arrangement is positioned through the sheet passageway W and the medication is administered. The plate adaptor 16 snugly embraces the section of the syringe and tube arrangement positioned through the sheet passageway W.

Aerosols generated by or around the patient P (which are considered as infectious for the purposes of this application) during administration of the medication or due to the patient P coughing or sneezing after revival or while being revived will be blocked by the sheet 12 and the snug engagement between the plate adaptor 16 and the section of the syringe and tube arrangement and prevented from escaping into the surrounding environment E and consequently reaching the health care worker and contaminating the health care worker. The system 10 thus forms a protective barrier between the patient P and the healthcare worker and acts as an additional layer of protection for the health care worker.

In a scenario and with reference to FIGS. 4 to 4B where the patient P needs resuscitation via a manual resuscitator 20, the health care worker first places a mask 20*a* of the resuscitator over the patient's nose and mouth area A. The sheet 12 is then operatively coupled to and supported on the resuscitator 20 for its positioning over and on the patient P. The sheet 12 is passed over a tubular stem 20*b* of the resuscitator 20, which connects the mask 20*a* to a bag element 20*c* of the resuscitator 20, through the sheet passageway W and the plate adaptor 16 is supported on a filter and valve element 20*d* of the resuscitator located on the stem 20*b*. The plate adaptor 16 snugly engages the stem 20*b*. The bag element 20*c* is then connected to an exposed end of the stem 20*b* projecting out from the plate adaptor 16 and the patient P is mechanically resuscitated by cyclically squeezing the bag element 20*c*. Again, aerosols that are generated by or around the patient P, during resuscitation, are blocked by the sheet 12 and snug engagement between the plate adaptor 16 and the stem 20*b* and prevented from escaping into the surrounding environment and contaminating the health care worker treating the patient P.

After use, the sheet 12 may be folded and re-inserted into the selabale bag 22 for disposal later. In another embodiment, instead of folding, the sheet 12 may be gathered by pulling on a drawstring 12*a* located around at least a portion of a periphery of the sheet 12 prior to its re-insertion into the bag 22.

The system described herein is lightweight and is, therefore, easy to transport or dispose of. The system has minimal components and is, therefore, very easy to handle and cost effective. The system does not occupy a large footprint and, therefore, can be effectively used in tight spaces.

The invention claimed is:

1. A protective barrier system for preventing spread of infectious aerosols, generated by or around a patient, into a surrounding environment when the patient is in a supine position and is being treated by a healthcare worker with a patient interface device, the system comprising:

a flexible, fluid-impervious sheet having preset longitudinal and transverse dimensions and adapted to cover at least an upper torso of the patient;

the sheet having a face portion which is adapted to cover at least a face of the patient, the face portion having an aperture which is adapted and dimensioned to, overlie at least a nose and mouth area of the patient, a plate adaptor made of a pliant non-porous material, mountable on the sheet to encircle the aperture, the plate adaptor comprising a corresponding adaptor aperture to form a passageway through the sheet, adaptor aperture being dimensioned to operatively couple to and form a snug engagement with the section of the interface device without gapping regardless of the size of the section of the interface device, wherein the plate adaptor includes an upper flange and a lower flange, the flanges configured to support the sheet therebetween and encircle the aperture on opposite sides of the sheet;

wherein, in use, when the sheet is positioned over and on the patient with the sheet covering at least the patient's upper torso including the face portion covering at least the patient's face and the aperture overlying at least the patient's nose and mouth area, the plate adaptor is mounted on the sheet to encircle the aperture, and the section of the interface device is positioned through the adaptor aperture, said adaptor aperture being dimensioned to form a snug engagement with the section of the interface device without gapping regardless of the size of the section of the interface device to block the infectious aerosols generated by or around the patient so as to prevent escape of the infectious aerosols into the surrounding environment and consequent contamination of the healthcare worker thereby forming a protective barrier between the patient and the healthcare worker.

2. The system of claim 1, wherein the transverse dimension is greater than a width of the patient's upper torso so as to enable the sheet to be tucked under at least the patient's upper torso for retainment of the sheet over and on the patient in the use position.

3. The system of claim 1, wherein the sheet further comprises one or more releasable fastener assemblies for retainment of the sheet over and on the patient in the use position.

4. The system of claim 1, wherein the sheet is a plastic sheet.

5. The system of claim 4, wherein the plastic sheet is clear.

6. The system of claim 1, wherein the sheet is a medical grade plastic sheet.

7. The system of claim 1 wherein the interface device is a manual resuscitator, and wherein the plate adaptor operatively couples to a tubular stem of the resuscitator without gapping and is supported on a filter and valve element located on the tubular stem for retainment of the sheet in the use position over and on the patient.

8. The system of claim 1 further comprising a sealable, fluid impermeable bag for storing at least the sheet prior to and after its use.

9. A method for preventing spread of infectious aerosols, generated by or around a patient, into a surrounding environment when the patient is in a supine position and is being treated by a healthcare worker with a patient interface device, the method comprising:

(a) covering at least an upper torso of the patient with the system of claim 1, such that the face portion of the sheet covers at least the face of the patient;

(b) aligning the aperture in the face portion with at least the patient's the nose and mouth area;

(c) mounting the plate adaptor on the sheet to encircle the aperture, and enabling passage of the section of the interface device to the patient's nose and mouth area through the adaptor aperture;

(d) forming a snug engagement between the adaptor aperture and the section of the interface device without gapping and using the sheet and the snug engagement between the adaptor aperture and the section of the interface device to block the infectious aerosols generated by and around the patient so as to inhibit escape of the infectious aerosols into the surrounding environment and consequent contamination of the healthcare worker by the infectious aerosols; and (d) mounting a plate adaptor to the sheet by:

(i) placing a lower flange of the plate adaptor beneath the sheet and aligning it with the aperture;

(ii) positioning an upper flange of the plate adaptor above the sheet so that the aperture of the sheet is fitted between the upper and lower flanges; and (iii) retaining the sheet between the upper and lower flanges such that the plate adaptor encircles the aperture and reinforces the sheet around the aperture to facilitate secure passage of the interface device through the aperture.

10. The method of claim 9 further comprising securing the sheet over and on the patient.

11. The method of claim 10, further comprising providing a plate adaptor mounted on and encircling the aperture, wherein the plate adaptor is adapted to operatively couple to the section of the interface device without gapping and be supported on the section of the interface device for securing the sheet over and on the patient.

* * * * *